(12) United States Patent
Pfrang

(10) Patent No.: US 11,351,311 B2
(45) Date of Patent: Jun. 7, 2022

(54) GLASS SYRINGE-SIDE ASSEMBLY AID ELEMENT, METHOD FOR FASTENING A GLASS SYRINGE-SIDE ASSEMBLY AID ELEMENT AND METHOD FOR PRODUCING A GLASS SYRINGE-SIDE ASSEMBLY AID ELEMENT, AS WELL AS AN ARRANGEMENT CONSISTING OF A GLASS SYRINGE AND AN ASSEMBLY AID ELEMENT

(71) Applicant: Gerresheimer Regensburg GmbH, Regensburg (DE)

(72) Inventor: Juergen Pfrang, Kallmuenz (DE)

(73) Assignee: GERRESHEIMER REGENSBURG GMBH, Regensburg (DE)

( * ) Notice: Subject to any disclaimer, the term of this patent is extended or adjusted under 35 U.S.C. 154(b) by 837 days.

(21) Appl. No.: 14/349,924

(22) PCT Filed: Oct. 30, 2012

(86) PCT No.: PCT/EP2012/071459
§ 371 (c)(1),
(2) Date: Apr. 4, 2014

(87) PCT Pub. No.: WO2013/072182
PCT Pub. Date: May 23, 2013

(65) Prior Publication Data
US 2014/0249479 A1    Sep. 4, 2014

(30) Foreign Application Priority Data

Nov. 15, 2011  (DE) .................... 10 2011 055 389.4

(51) Int. Cl.
*A61M 5/32*    (2006.01)
*A61M 5/34*    (2006.01)
(Continued)

(52) U.S. Cl.
CPC .............. *A61M 5/343* (2013.01); *A61M 5/24* (2013.01); *A61M 5/3129* (2013.01);
(Continued)

(58) Field of Classification Search
CPC ........ A61M 5/3134; A61M 2005/3103; A61M 2005/3118; A61M 2005/3109;
(Continued)

(56) References Cited

U.S. PATENT DOCUMENTS 3,605,743 A    9/1971  Arce
4,009,716 A *  3/1977  Cohen ................... A61M 5/288
                                                      604/201

(Continued)

FOREIGN PATENT DOCUMENTS

CN    1864758 A     11/2006
CN    201832234 U    5/2011
(Continued)

OTHER PUBLICATIONS

International Search Report, International Application No. PCT/EP2012/071459, English Language, dated Jan. 23, 2013, 3 pages.

(Continued)

*Primary Examiner* — William R Carpenter
*Assistant Examiner* — William R Frehe
(74) *Attorney, Agent, or Firm* — Leydig, Voit & Mayer, Ltd.

(57) ABSTRACT

The invention relates to a glass syringe-side assembly element for providing an interface element between a glass syringe including on its front side a syringe cone part with a syringe needle and including on its rear side a flange part and a glass syringe operating means, where the assembly element can be arranged on the outer contour of the glass syringe, and where the assembly element can be secured to the assembly element relative to the syringe needle in front (Continued)

of the flange part on the glass syringe such that a reference point of the assembly element is always at a defined distance from the needle tip of the syringe needle.

25 Claims, 5 Drawing Sheets

(51) Int. Cl.
*A61M 5/24* (2006.01)
*A61M 5/46* (2006.01)
*A61M 5/315* (2006.01)
*A61M 5/31* (2006.01)

(52) U.S. Cl.
CPC ...... *A61M 5/31511* (2013.01); *A61M 5/3213* (2013.01); *A61M 5/349* (2013.01); *A61M 5/46* (2013.01); *Y10T 29/49826* (2015.01); *Y10T 156/10* (2015.01)

(58) Field of Classification Search
CPC .. A61M 5/3202; A61M 5/3204; A61M 5/343; A61M 5/3129; A61M 5/349; A61M 5/31578; A61M 2005/3104; A61M 2205/6045; A61M 2005/14553; A61M 5/3271; A61M 5/3272; A61J 1/00
See application file for complete search history.

(56) References Cited

U.S. PATENT DOCUMENTS

| | | | | |
|---|---|---|---|---|
| 4,022,207 A | * | 5/1977 | Citrin | A61M 5/20 604/209 |
| 4,518,387 A | | 5/1985 | Murphy et al. | |
| 4,929,232 A | * | 5/1990 | Sweeney | A61M 5/5086 604/111 |
| 4,948,000 A | * | 8/1990 | Grabenkort | A61J 1/00 206/438 |
| 5,292,318 A | * | 3/1994 | Haber | A61M 5/31551 604/407 |
| 2004/0015136 A1 | * | 1/2004 | Stewart | A61M 5/3271 128/919 |
| 2004/0236284 A1 | * | 11/2004 | Hoste | A61M 5/326 604/198 |
| 2006/0167412 A1 | * | 7/2006 | Marshall | A61M 5/326 604/110 |
| 2009/0234297 A1 | * | 9/2009 | Jennings | A61M 5/2033 604/195 |
| 2009/0312707 A1 | * | 12/2009 | Bishop | A61M 5/24 604/135 |

FOREIGN PATENT DOCUMENTS

| | | |
|---|---|---|
| EP | 1 462 134 A1 | 9/2004 |
| WO | WO 93/10838 A1 | 6/1993 |
| WO | WO 01/07105 A1 | 2/2001 |
| WO | 2004/108194 | 12/2004 |

OTHER PUBLICATIONS

Office Action corresponding to Chinese Patent Application No. 201280050897.8, dated Jul. 3, 2015—Search Results Only.
European Examination Report, dated Feb. 7, 2017, in European patent application serial No. 12786875.0, a related application, 2 pp.
EP Fifth Office Action, dated Dec. 12, 2018 in European Patent Application No. 12786875.0, a related application, 3 pp.

* cited by examiner

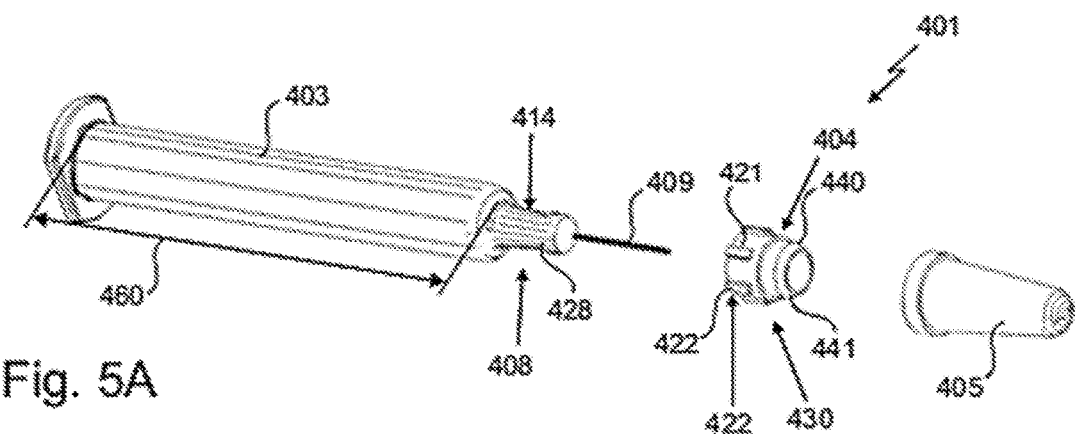
Fig. 5A
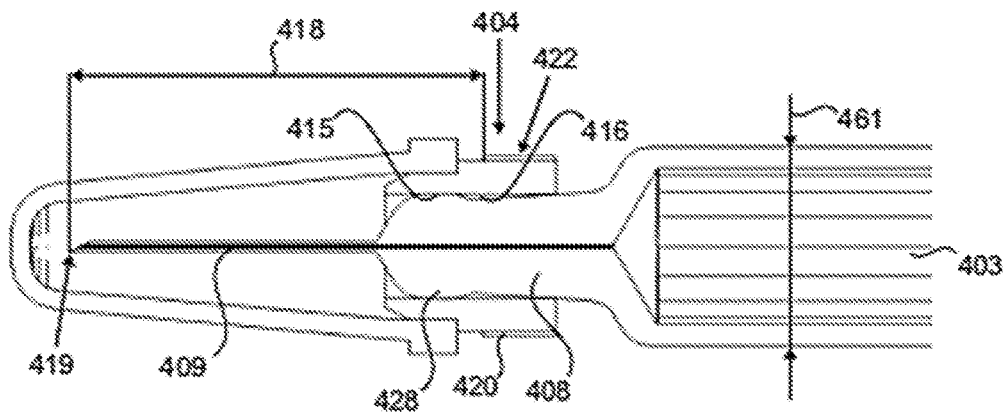
Fig. 5B
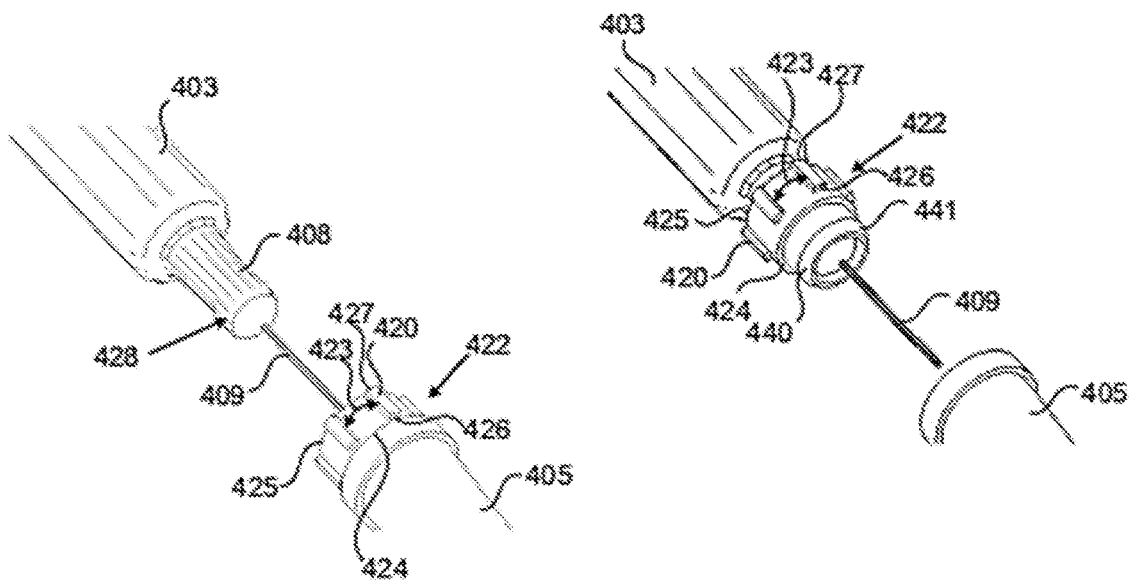
Fig. 5C
Fig. 5D

GLASS SYRINGE-SIDE ASSEMBLY AID ELEMENT, METHOD FOR FASTENING A GLASS SYRINGE-SIDE ASSEMBLY AID ELEMENT AND METHOD FOR PRODUCING A GLASS SYRINGE-SIDE ASSEMBLY AID ELEMENT, AS WELL AS AN ARRANGEMENT CONSISTING OF A GLASS SYRINGE AND AN ASSEMBLY AID ELEMENT

CROSS REFERENCE TO RELATED APPLICATIONS

This application is a U.S. National Stage Application under 35 U.S.C. § 371 of International Application No. PCT/EP2012/071459, filed Oct. 30, 2012, which claims the benefit of and priority to German Application No. 10 2011 055 389.4, filed on Nov. 15, 2011, each of which is hereby incorporated by reference in its entirety.

The invention relates to a glass syringe-side assembly element for providing an interface element between a glass syringe comprising on its front side a syringe cone part with a syringe needle and comprising on its rear side a flange part and a glass syringe operating means, wherein the assembly element can be arranged on the outer contour of the glass syringe.

Furthermore, the invention relates to a glass syringe-side assembly element for providing an interface element between a glass syringe and a glass syringe operating means, wherein the assembly element can be arranged on the outer contour of the glass syringe.

The invention also relates to a method for securing a glass syringe-side assembly element onto a glass syringe.

The invention also relates to a method for producing a glass syringe-side assembly element for providing an interface element between a glass syringe and a glass syringe operating means.

Furthermore, the invention relates to an arrangement consisting of a glass syringe and an assembly element for providing an interface element between a glass syringe comprising on its front side a syringe cone part with a syringe needle and comprising on its rear side a flange part and a glass syringe operating means.

Generic glass syringes are widely used, particularly as all-glass syringes. Glass syringes of this kind are used for historical reasons but are also designed as stand-alone devices for manufacturing reasons. However, they are being used increasingly in connection with other medical devices, such as for example injectors, safety devices or the like. However, their use on or respectively in medical devices of this kind turns out to be very complex in most cases, as the manufacturers of such devices generally have to modify the latter with adapters in a complex manner in order in particular to use different types of glass syringe thereon. Even if a suitable adapter is provided, the assembly of the glass syringes with respect to said medical devices often proves complex as it is essentially a one-off solution.

The object of the present invention is to provide a structurally simple interface between a conventional glass syringe and a glass syringe operating means, by means of which conventional glass syringes can be mounted simply and rapidly on the glass syringe operating means and can be used more reliably with the latter.

The object of the invention is achieved by a glass syringe-side assembly element for providing an interface element between a glass syringe comprising on its front side a syringe cone part with a syringe needle and comprising on its rear side a flange part and a glass syringe operating means, wherein the assembly element can be arranged on the outer contour of the glass syringe, and wherein the assembly element comprises a securing means in order to secure the assembly element relative to the syringe needle in front of the flange part on the glass syringe in such a way that a reference point of the assembly element is always at a defined distance from the needle tip of the syringe needle.

In the case of assembly elements known previously from the prior art, the securing position thereof on the glass syringe is so inconvenient on the rear flange of the glass syringe that, on the one hand, there is risk of over-stressing the glass syringe which often causes the glass to break and thus also destroys the glass syringe. It is therefore advantageous that the securing position is positioned relative to the syringe needle in front of said flange according to the invention. On the other hand, the assembly element is advantageously always secured to the glass syringe in such a way that a reference point of the assembly element according to the invention is always a defined distance from the syringe needle tip. In this way a particularly high degree of operating safety is achieved when handling the glass syringe as the external part of the glass syringe that has a very high tolerance in manufacturing terms can be provided structurally in a simple and inexpensive manner compared to medical devices or respectively glass syringe operating means with a defined interface, whereby the position of the syringe needle inside a medical device or respectively a glass syringe operating means is defined in an exceptionally precise and reliable manner. Thus, in practice a desired insertion depth of the syringe needle is always ensured very precisely.

The term "reference point" describes within the meaning of the invention a point or an area on the assembly element, which is always arranged at the same distance or respectively in the same position axially as well as radially relative to the syringe needle tip. Axially refers here to the longitudinal extension of the glass syringe, radially means perpendicularly thereto. In the simplest case the reference point is formed by an edge of the assembly element.

The assembly element is arranged permanently on the glass syringe within the meaning of the invention. For this purpose, in particular the securing methods described below can be used in an advantageous manner.

Advantageously, a securing point of the securing means is spaced apart by more than 5 mm, preferably by more than 10 mm, from the flange of the glass syringe, so that in particular the risk of the glass breaking because of a critical increase in tension can be reduced further.

In general terms, the present assembly element ensures an exceptionally safe securing of the glass syringe on additional devices, in particular on glass syringe operating means, such as injectors, safety devices, needle shields or the like.

In order to use the present assembly element comprising the glass syringe in a defined manner and thereby without any difficulty in such glass syringe operating means and to be able to operate it on the latter, it is advantageous if the assembly element comprises a holding device for holding on the glass syringe operating means.

Preferably, the holding device is arranged on the outer peripheral side of the assembly element. However, it can also be positioned increasingly or alternatively on the head side of the assembly element. Of course, the holding device can also be configured to be specific to the device. Preferably, the holding device is configured to be standardised so that the production and application thereof can be simplified further. For example, the holding device has a specific external structure, for example in the form of a tongue-and-groove configuration, wherein the said grooves or respectively tongues can be arranged in the circumferential and/or longitudinal direction of the assembly element. If necessary a thread structure can be provided as an alternative. Of course, a counter structure is provided on the respective glass syringe operating means interacting therewith.

In any case, it is advantageous if the assembly element has an overall external geometry which is defined exactly with regard to its dimensions and in particular its distance from the needle tip, but also relative to the flange of the glass syringe.

In a first particularly preferred embodiment variant, the securing means comprises a mounting area for mounting the syringe cone part, in order to secure the assembly element onto the syringe cone part and thus onto the glass syringe.

The syringe cone part is particularly stable because of its relatively high proportion of glass material and is thus less prone to breaking. As the syringe needle is also embedded there, the syringe cone part is located in the immediate proximity of the syringe needle. Both of these factors mean that the syringe cone part is particularly suitable as a securing point for the present assembly element within the meaning of the invention.

Thus the features relating to securing the assembly element onto the syringe cone part are a further development of previously known adapters even without the remaining features of the invention and are thus particularly advantageous independently of these other features.

If the securing means has a peripheral groove for arranging a peripheral elevation of the syringe cone part, an excellent seal can also be obtained between the assembly element and the syringe cone part. Said groove can be formed only when injection-moulding or welding the assembly element onto the syringe cone part through the peripheral elevation.

According to a further particularly preferred embodiment variant, the securing means comprises a mounting area for mounting a shoulder region of the glass syringe in order to secure the assembly element onto the shoulder region and thereby onto the glass syringe.

The shoulder region of the glass syringe also provides a relatively stable and unbreakable securing point on the glass syringe to which the present assembly element can be secured extremely precisely. Therefore, the risk that the glass of the syringe will break in the shoulder region is also considerably reduced compared to conventional securing positions.

It is also possible to attach the assembly element successively onto said shoulder region of the glass syringe and thereby advantageously onto the glass syringe.

At this point it should also be noted that the features relating to securing the assembly element onto the shoulder region of the glass syringe are a further advantageous development of previously known adapters even without the remaining features of the invention. Thus, the object of the invention is already achieved by said features with regard to the securing.

With regard to another particularly preferred embodiment variant, it is possible in an advantageous manner for the securing means to comprise a mounting area for mounting a cylinder region of the glass syringe, wherein the cylinder region has a longitudinal extension that is larger than its diameter in order to secure the assembly element to the cylinder region and thus to the glass syringe.

Advantageously, by means of such a cylinder region a securing point can be provided on the glass syringe which forms the largest possible bearing surface so that forces can be transmitted between the assembly element and the glass syringe over a particularly large area. In this way the risk of the glass of the syringe breaking can be reduced increasingly or alternatively. Similarly, in this case a defined positioning of the assembly element relative to the syringe needle can be achieved in an advantageous manner.

Thus, the features relating to securing the assembly element onto the cylinder region are a further development of previously known adapters even without the other features of the invention and are thus also particularly advantageous independently of said additional features.

Preferably, the cylinder region lies between the shoulder region and the flange part of the glass syringe, so that the assembly element is also arranged in this case in front of the flange. The term "cylinder region" thus describes a substantially cylindrical section of the glass syringe, which lies between the shoulder region and the flange part.

In this connection it should be mentioned that the term "shoulder region" describes a section of the glass syringe in which the glass syringe widens radially out from the syringe cone part and passes into the cylinder region of the glass syringe.

According to a further aspect of the invention, the present object is also achieved by a glass syringe-side assembly element for providing an interface element between a glass syringe and a glass syringe operating means, wherein the assembly element can be arranged on the outer contour of the glass syringe, wherein the assembly element comprises an inner contact area facing the glass syringe and a glass syringe operating means contact area facing away from the glass syringe, and wherein the inner contact area is designed to be softer than the glass syringe operating means contact area.

As the inner contact area of the assembly element has softer material properties, the assembly element can fit much more snugly against the glass syringe, whereby the interaction between these two components can be extremely intensive. This alone makes it possible to achieve a considerable reduction of the risk that the glass of the syringe might break.

In this connection, the object of the invention is also achieved by a method for producing an assembly element for providing an interface element between a glass syringe and a glass syringe operating means, in which the assembly element is made from at least two layers, whereby it is designed to be softer on the side facing the glass syringe than on one of the sides facing away from the glass syringe, on which the glass syringe operating means is arranged.

In this way, within the meaning of the invention a particularly advantageous multi-component part can be provided easily in terms of process engineering.

In addition, the assembly element can be developed further particularly advantageously with respect to patient and occupational safety, if the assembly element comprises a protective cap part for covering the syringe needle, which cap part is arranged by means of a predetermined breaking point on the assembly element. The protective cap part can in this way form a multifunctional needle-shield which, on the one hand, can ensure the safety and shielding function of a needle tip. On the other hand, the assembly element can connect with its rear proximal end which, after the removal of the protective cap part, remains on the glass syringe. A particularly simple removal or respectively release of the protective cap part from the assembly element can be ensured by the predetermined breaking point.

Advantageously, the assembly element is made of plastics material or a composite thereof. Other embodiment variants can however also provide that the assembly element is made of metal or a metal alloy. Of course, other easily shaped and mouldable materials can also be used.

The object of the invention is also achieved according to another aspect by a method for securing an assembly element onto a glass syringe, in which a securing means of the assembly element is attached relative to a syringe needle of the glass syringe in front of a flange part of the glass syringe externally onto the glass syringe, in that the securing means is injection-moulded onto the outer contour of the glass syringe.

By means of this injection-moulding of the securing means onto the outer contour of the glass syringe, on the one hand, the joint geometry of the assembly element or respectively the securing means can be adjusted exactly to the highly tolerant external form of the glass syringe. On the other hand, in terms of manufacturing technology almost any conceivable and practicable holding device geometry can be provided for holding in the glass syringe operating means.

However, it is possible that when injecting around the glass syringe, a specific seal of an insertion part is necessary, which also withstands internal pressure on the injection tool but can reduce or respectively completely eliminate the risk of the glass of the syringe breaking. In an advantageous manner said insertion part can also form the aforementioned softer inner contact area of the assembly element.

A further variant of the method independent of the other features of the invention ensures in an advantageous manner that a securing means of the assembly element is attached relative to a syringe needle of the glass syringe in front of a flange part of the glass syringe externally on the glass syringe, in that the securing means is adhered to the outer contour of the glass syringe.

In this case, any adhesive suitable for medical purposes can be used. In particular, UV-curing adhesives can also be used in an advantageous manner which, being quick setting, can provide a snug connection directly on the actual contact surface between the assembly element and the glass syringe.

However, it is particularly advantageous if the attachment is achieved by means of an adhesive label or the like. The use of such adhesive labels is known from the prior art for other purposes, such as for example with respect to adhered injection needle cover devices, and has already been proved effective in practice. In particular, by means of the preferred adhesive label the joint geometry of the assembly element or respectively the securing means can be adapted easily to the highly tolerant external configuration of the glass syringe. On the basis of this very simple procedure, fastening by means of an adhesive label is preferred in this case over other securing methods.

In an alternative but no less advantageous variant of the method, a securing means of the assembly element is attached relative to a syringe needle of the glass syringe in front of a flange part of the glass syringe externally on the glass syringe, in that the securing means is welded onto the outer contour of the glass syringe.

The assembly element can also advantageously be secured to the glass syringe by means of an ultrasound or laser welding method for example. Furthermore, in this way by melting on the assembly element material, the joint geometry of the assembly element or respectively the securing means can be adjusted very effectively to the highly tolerant external form of the glass syringe.

Furthermore, the object of the invention is also achieved by an arrangement consisting of a glass syringe and an assembly element for providing an interface element between the glass syringe comprising on its front side a syringe cone part with a syringe needle and comprising on its rear side a flange part and a glass syringe operating means, in which the assembly element is secured relative to the syringe needle in front of the flange part on the glass syringe such that a reference point of the assembly element always has a defined distance or respectively the same position axially as well as radially to the syringe needle tip, wherein the assembly element is injection moulded, adhered or welded onto the glass syringe.

In summary, all of the present, achievable advantages of the invention can also be maintained for the latter arrangement as follows. Firstly, the risk that the glass of the glass syringe will break is avoided as the assembly element is not secured via the flange of the glass syringe. Secondly, a much better definition of the syringe needle insertion depth is achieved by bypassing the tolerance by means of the assembly element. Thirdly, there is no need for costly individual interface solutions for the medical devices, if necessary in this way a uniform industrial standard can be created. Fourthly, the production costs of the whole system consisting of a glass syringe and glass syringe operating means are considerably reduced. Fifthly, an advantageous combination solution of an assembly element with a protective cap part can be provided for a needle-shield function.

Advantageously, the arrangement comprises an assembly element according to any of the features described herein.

Further advantages, objectives and properties of the present invention are explained with reference to the attached drawings and the following description, in which by way of example several glass syringe-side assembly elements are illustrated and described in an arrangement with a glass syringe. In the drawings:

FIG. 5A shows schematically a further exploded view of an alternative arrangement of a glass syringe and an assembly element secured thereon on the syringe cone part side;

FIG. 5B shows schematically a longitudinal section of a detailed view of the alternative arrangement of FIG. 5A in an assembled state;

FIG. 5C shows schematically a perspective view of the not yet secured assembly element of FIGS. 5A and 5B with a fitted protective cap part;

FIG. 5D shows schematically a perspective view of the secured assembly element of FIGS. 5A to 5C with a protective cap part removed from the assembly element;

Figures 1A, 1B:
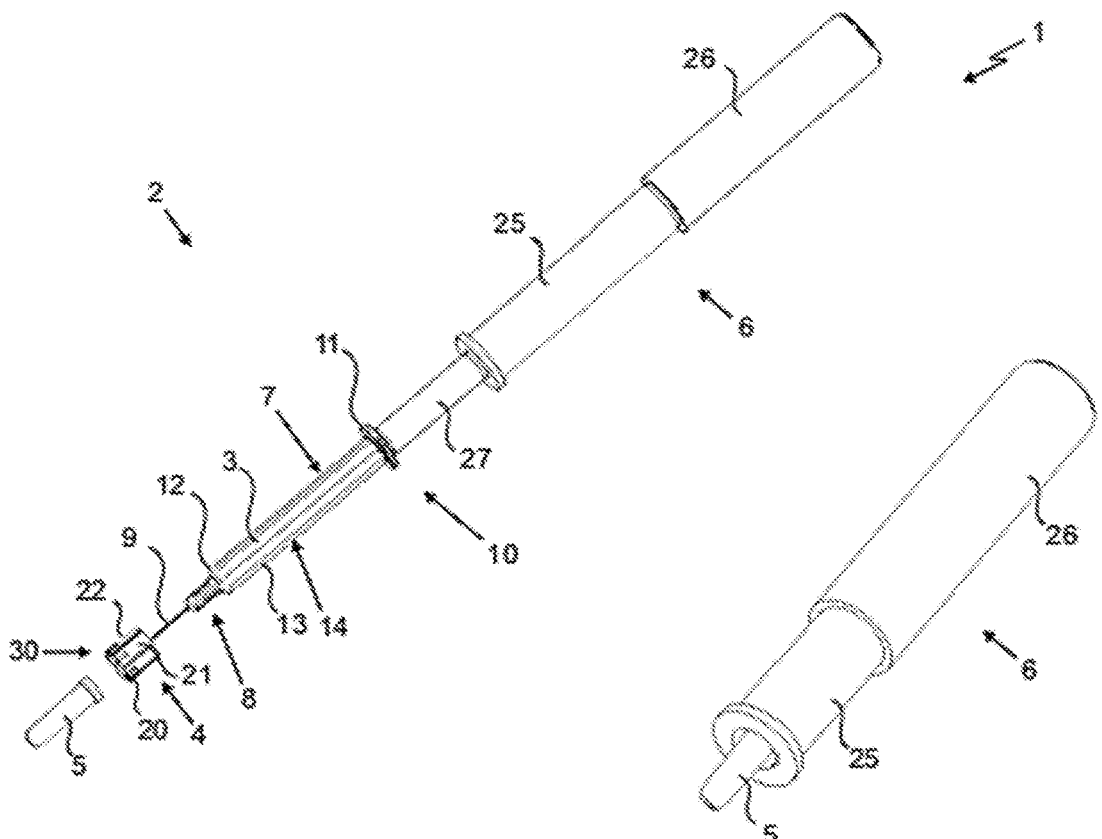
FIG. 1A shows schematically an exploded view of an arrangement consisting of an assembly element, a glass syringe and a glass syringe operating means.
FIG. 1B shows schematically a further view of the arrangement of FIG. 1A in an assembled state.

The first embodiment 1 illustrated in FIGS. 1A to 1D shows a first arrangement 2 consisting of a commercially available glass syringe 3, an assembly element 4, a protective cap part 5 and a glass syringe operating means 6.

The glass syringe 3 comprises a base body 7 with a front side syringe cone part 8, by means of which a syringe needle 9 is arranged embedded on the base body 7 of the glass syringe 3. The base body 7 further comprises a flange part 11 at the rear end 10 of the glass syringe 3. Between the syringe cone part 8 and the flange part 11 are a shoulder region 12 and a cylinder region 13. The cylinder region 13 comprises a longitudinal extension 60 and diameter 61. As a whole the syringe cone part 8, the shoulder region 12, the cylinder region 13 and the flange part 11 define the outer contour 14 of the glass syringe 3.

The assembly element 4 comprises a securing means 15 (cf. in particular FIGS. 1C and 1D) with an inner contact area 16 which faces the glass syringe 3. By means of the securing means 15 the assembly element 4 is secured to the glass syringe 3.

The assembly element 4 also comprises, in the circumferential direction, a plurality of reference points (not numbered here), by means of which a defined distance 18 from the needle tip 19 of the syringe needle 9 can always be ensured.

The reference points can for example be provided by means of spring elements 20 of a holding device 21, by means of which the glass syringe operating means 6 can be supported on the assembly element 4. The spring elements 20 are provided in this case in a glass syringe operating means contact area 22 on the outside of the assembly element 4, the spring elements 20 interacting with corresponding grooves (not numbered here) of the glass syringe operating means 6 in the manner of a tongue-and-groove connection.

The glass syringe operating means 6 consists at least in this first embodiment 1 of a holding part 25, on which a pushing element 26 with a plunger element 27 is mounted so as to move in a translatory manner.

On the syringe cone part 8 a peripheral elevation 28 is provided. In this first embodiment 1, the protective cap part 5 can be held securely on the latter.

Figure 1C:
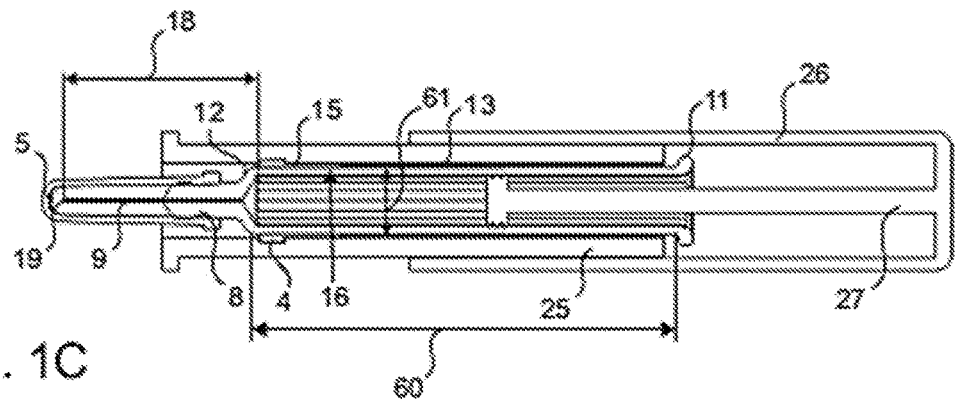
FIG. 1C shows schematically a longitudinal cross-sectional view of the arrangement of FIGS. 1A and 1B.
Figure 1D:
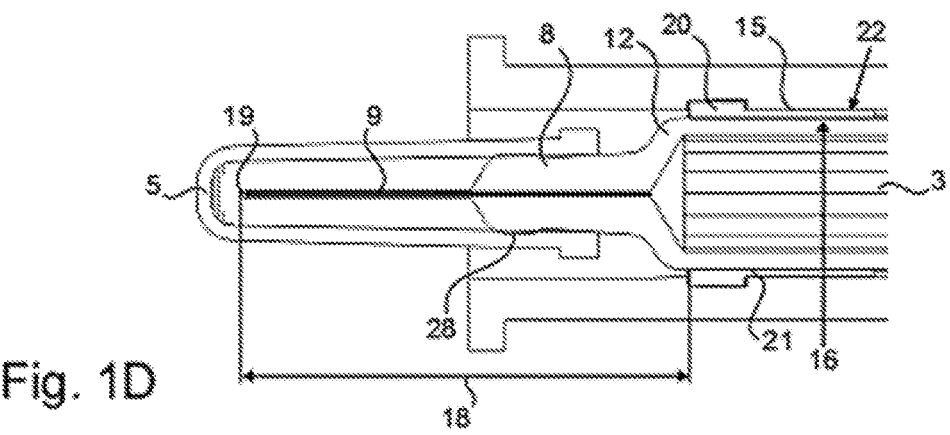
FIG. 1D shows schematically a longitudinal section of a detailed view of the arrangement of FIGS. 1A to 1C relating to a part of the syringe cone of the glass syringe.

In FIGS. 1B to 1D the arrangement 2 is shown in the as-delivered condition, in which the glass syringe operating means 6 has not yet been activated and the protective cap part 5 is still fitted onto the syringe cone part 8.

The assembly element 4 provides a particularly advantageous interface element 30 between the glass syringe 3 and the glass syringe operating means 6.

Figure 2A:
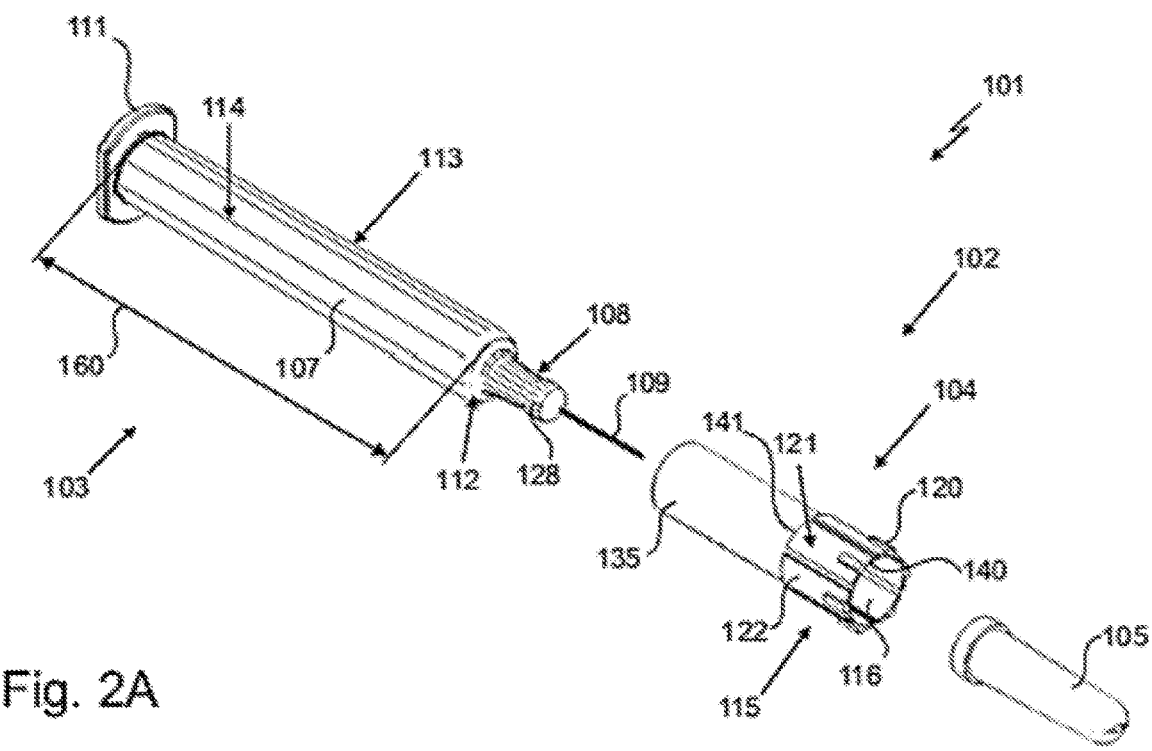
FIG. 2A shows schematically an exploded view of a further arrangement of a glass syringe and an assembly element secured thereon on the cylinder region.
Figure 2B:
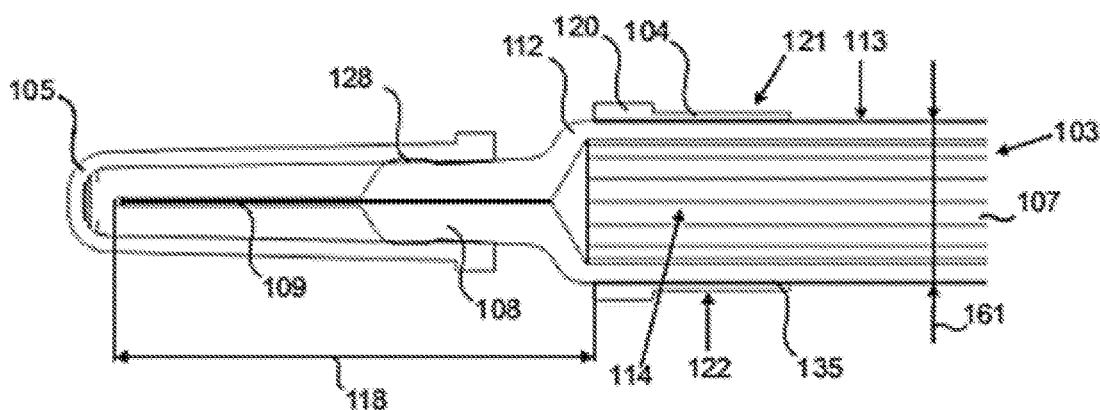
FIG. 2B shows schematically a longitudinal section of a detailed view of the arrangement of FIG. 2A in an assembled state.
Figure 2C:
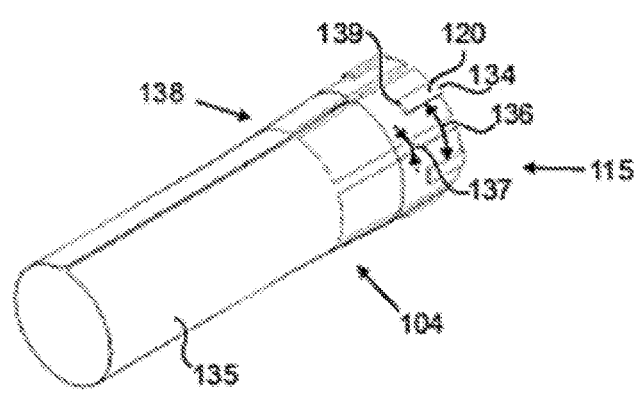
FIG. 2C shows schematically a perspective view of the assembly element of FIGS. 2A and 2B.

The second embodiment 101 illustrated in FIGS. 2A to 2C shows an arrangement 102 consisting of a commercially available glass syringe 103, an assembly element 104 and a protective cap part 105, wherein the glass syringe 103 comprises a base body 107 with a front-side syringe cone part 108, by means of which a syringe needle 109 is arranged embedded on the glass syringe 103. The base body 107 further comprises a flange part 111 at its rear end 110. Between the syringe cone part 108 and the flange part 111 are again arranged a shoulder region 112 and a cylinder region 113 of the glass syringe 103. The cylinder region 113 comprises a longitudinal extension 160 and diameter 161.

The assembly element 104 comprises a securing means 115 with an inner contact area 116 which faces the glass syringe 103. In this case the assembly element 104 is secured by the securing means 115 to the glass syringe 103 (cf. FIG. 2B). Furthermore, it comprises a plurality of reference points in the circumferential direction in the form of spring elements 120, by means of which a defined distance 118 to the needle tip 119 of the syringe needle 109 is always ensured.

The spring elements 120 are provided by a holding device 121 by means of which a glass syringe operating means (cf. FIG. 1) is supported on the assembly element 104. The spring elements 120 are provided in a glass syringe operating means contact area 122 on the outside of the assembly element 104.

As can easily be seen, the assembly element 104 is also secured here in the cylinder region 113 of the glass syringe 103, the assembly element 104 being secured by a partly double-sided adhesive label 135 to the glass syringe 103. For this purpose, the partly double-sided adhesive label 135 is simply adhered onto the outer contour 114 of the glass syringe 103.

Thus the assembly element 104 again provides here a structurally advantageous interface element 130 for the glass syringe 103.

On the syringe cone part 108 a peripheral elevation 128 is provided. The protective cap part 105 can be securely attached to the latter.

Figure 3:
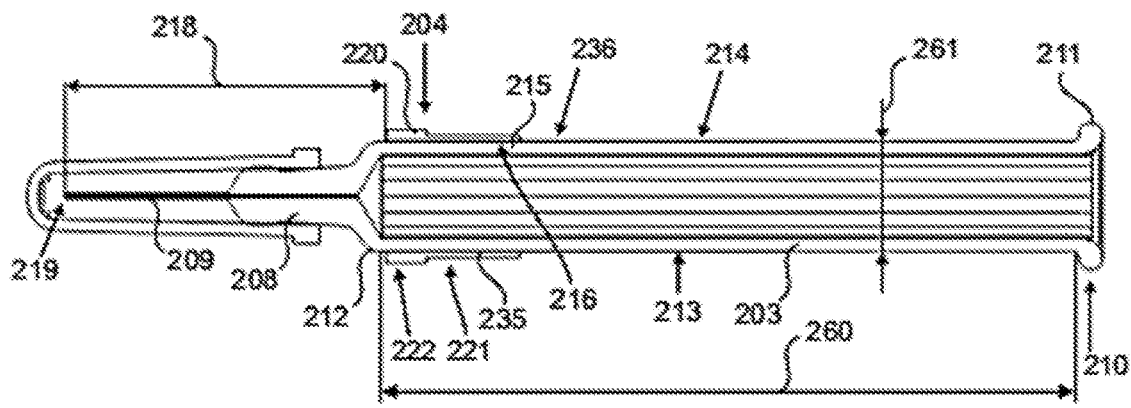
FIG. 3 shows schematically a longitudinal section of a similar arrangement of a glass syringe and a similar assembly element secured thereon in the cylinder region as in FIGS. 2A to 2C.

The additional assembly element 204 shown in FIG. 3 corresponds substantially in terms of its structure to the assembly element 104 of FIG. 1 and it is also secured by means of a single-sided adhesive label 235 to a glass syringe 203, likewise in a cylinder region 213 of the glass syringe 203.

However, the assembly element 204 flattens out further in the rear area 236 so that an even flatter transition is created to the glass syringe 203 than is the case in the previous embodiments. If necessary the assembly element 204 can be secured more advantageously in an improved manner to the glass syringe 203 by an additional securing means using a tape (not shown here) wound up to the outer contour 214 of the glass syringe 203.

Otherwise, the assembly element 204 comprises a securing means 215 with an inner contact area 216 in order to adhere a large area with the adhesive label 235. On the outside of the assembly element 204, a holding device 221 is provided for holding a glass syringe operating means on a glass syringe operating means contact area 222 which in turn comprises spring elements 220 for establishing a tongue-and-groove connection between the assembly element 204 and the glass syringe operating means.

The spring elements 220 again define reference points on the assembly element 204, by means of which a defined distance 218 between the assembly element 204 and a needle tip 219 can be determined.

The glass syringe 203 again has a structure with a base body 207, which comprises on the front side a syringe cone part 208 with a syringe needle 209, a shoulder region 212 adjoining the latter, the following cylinder region 213 and a flange part 211 at the end 210 of the glass syringe 203. The cylinder region 213 again comprises a longitudinal extension 260 and diameter 261.

Figure 4A:
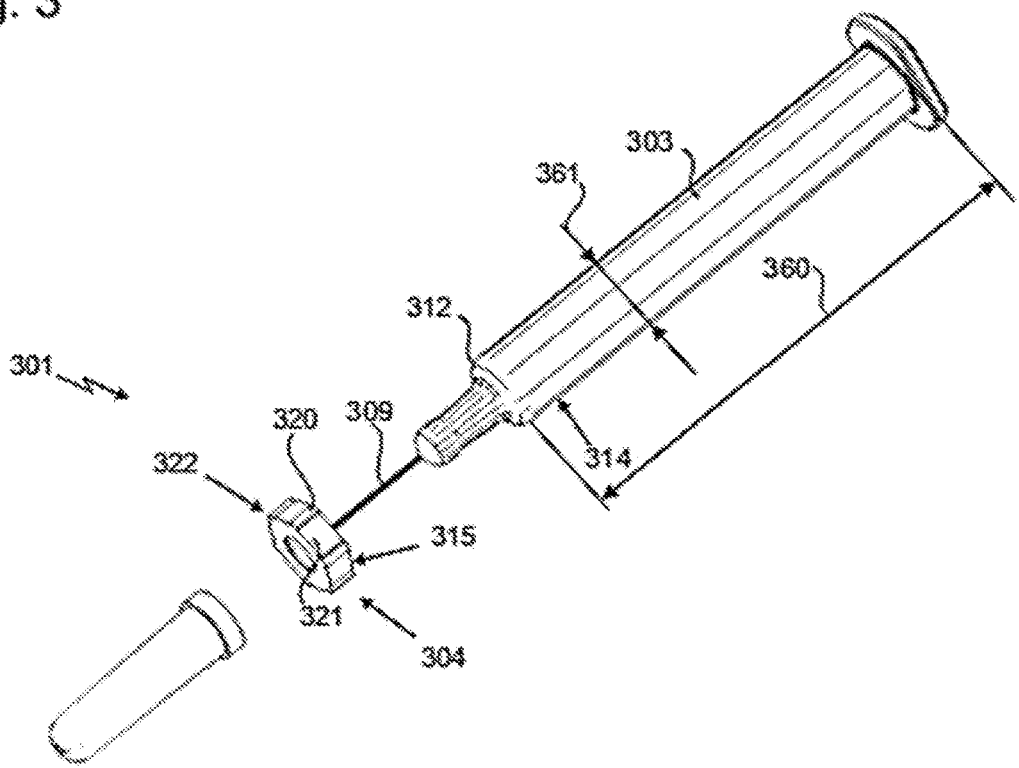
FIG. 4A shows schematically an exploded view of another arrangement of a glass syringe and an assembly element secured thereon in the shoulder region.
Figure 4B:
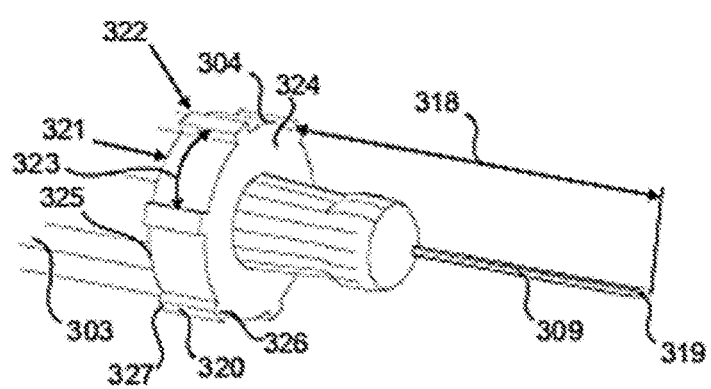
FIG. 4B shows schematically a perspective detailed view of the arrangement of FIG. 4A in an assembled state.

The further embodiment 301 shown in FIGS. 4A and 4B again consists of a glass syringe 303 of the aforementioned type and to avoid repetition a detailed description is not given here. In any case the glass syringe 303 comprises a shoulder region 312 on which an assembly element 304 is injection-moulded. Thus, the assembly element 304 is provided on the inner side with a securing means 315 by means of which it can be secured to the shoulder region 312 and thus without difficulty to an outer contour 314 of the glass syringe 303. Also in this way a defined distance 318 can be obtained between the assembly element 304 and a needle syringe 319 of a syringe needle 318 by way of reference points in the form of spring elements 320. The spring elements 320 belong, as in the embodiments explained above, also to a tongue-and-groove connection between a glass syringe operating means contact area 322 of an assembly element-side holding device 321 and a glass syringe operating means not shown here.

In the next embodiment 401 shown in FIGS. 5A to 5D, an assembly element 404 is welded advantageously to a syringe cone part 408 of a glass syringe 403. As the glass syringe 403 in this next embodiment 401 is identical to the previously described glass syringes, only essential differences from the above embodiments are described here.

As can be seen clearly in the representation of FIG. 5B, the assembly element 404 sits with a securing means 415 on the syringe cone part 408 and a peripheral elevation 428 formed there, in order to secure the assembly element 404 to the syringe cone part 408 and thus to an outer contour 414 of the glass syringe 403 in an advantageous manner.

For this purpose an inner contact area 416 has been melted on by means of a laser welding method so that the assembly element 404 is connected in an advantageous manner particularly closely to the syringe cone part 408.

The assembly element 404 again has on the outside a holding device 421 for holding on a glass syringe operating means not shown here. The assembly element 404 or respectively the holding device 421 comprises a glass syringe operating means contact area 422 with spring elements 420 for establishing a tongue-and-groove connection.

Furthermore, there is again a defined distance 418 between the assembly element 404 and the needle tip 419 of a syringe needle 409 of the glass syringe 403.

In this respect the assembly element 404 represents a further advantageous interface element 430 on the glass syringe 403.

Unlike the embodiments explained above, a protective cap part 405 is not arranged on the syringe cone part 408 as the assembly element 404 is positioned there. For this reason, the assembly element 404 is characterised by an attachment device 440 for fitting the protective cap part 405 onto the assembly element 404. The attachment device 440 comprises a front concentric bulge 441 of an undercut element behind which the protective cap part 405 can engage.

According to the representation shown in FIG. 5C, the assembly element 404 fitted with the protective cap part 405 has not yet been melted onto the syringe cone part 408 of the glass syringe 403 by the laser welding method.

According to the representation shown in FIG. 5D, the protective cap part 405 has been removed from the now fully assembled assembly element 404 and the glass syringe 403 with the assembly element 404 is ready for use.

Figure 6A:
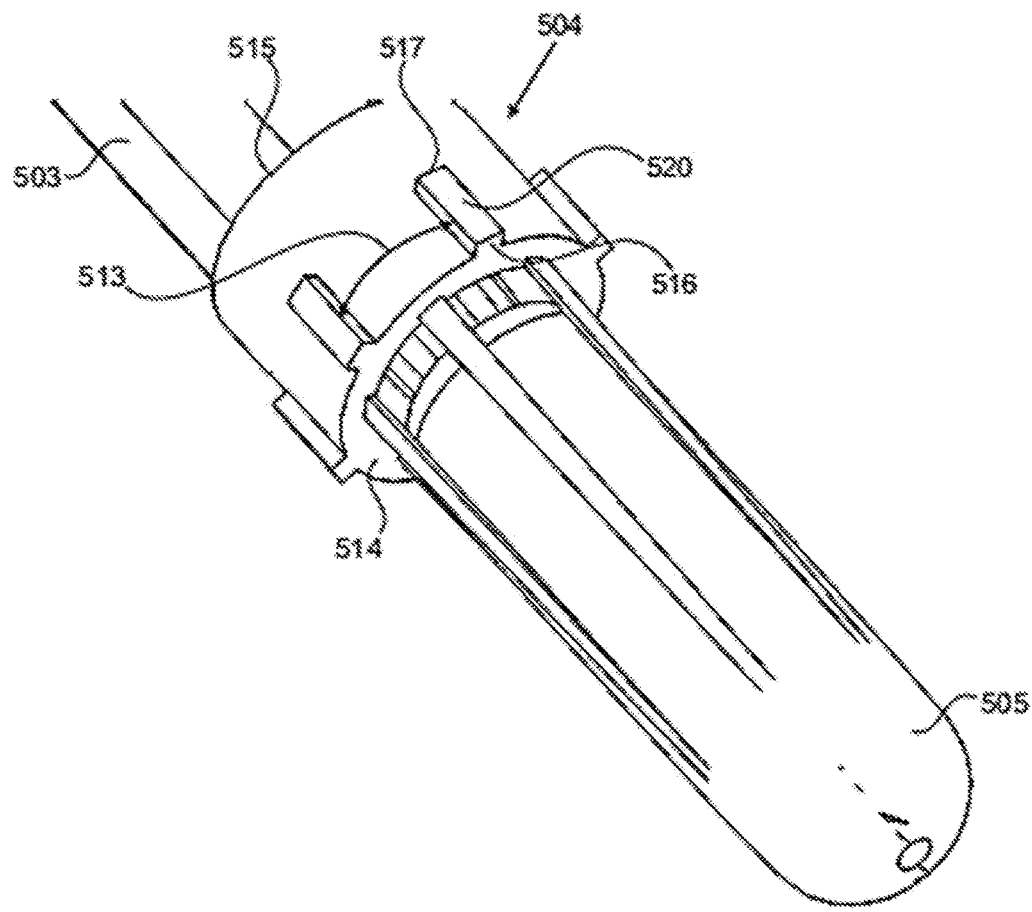
FIG. 6A shows schematically a perspective view of an assembly element with a protective cap part arranged thereon by a predetermined breaking point for covering a syringe needle.
Figure 6B:
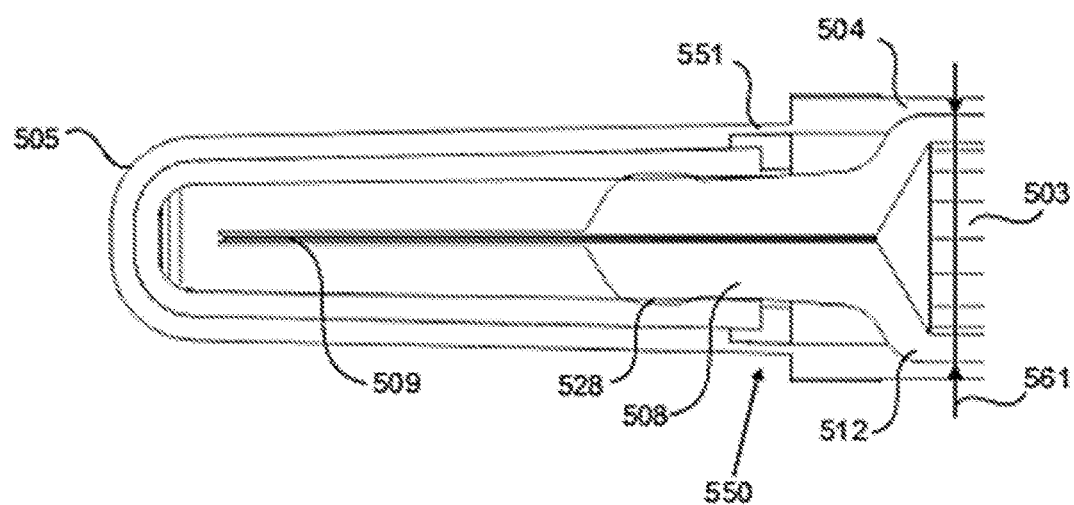
FIG. 6B shows schematically a longitudinal section of the assembly element of FIG. 6A.

In the assembly element 504 shown in FIGS. 6A and 6B, which is injection-moulded onto a shoulder region 512 of a glass syringe 503, a protective cap part 505 for covering a syringe needle 509 is secured by means of a thin peripheral connecting web 550 to the assembly element 504. The thin connecting web 550 is a predetermined breaking point 551 which means, on the one hand, that the protective cap part 505 can be provided preassembled in a secure manner. On the other hand, the secured protective cap part 505 can be separated easily from the assembly element 504 by means of the predetermined breaking point 551. In addition, the protective cap part 505 is mounted on a peripheral elevation 528 of a syringe cone part 508 of the glass syringe 503, so that it can also be secured back onto the glass syringe 503 after the connecting web 550 is broken.

Of course, the embodiments explained above are only first configurations of glass syringe-side assembly elements according to the invention. The design of the invention is not limited to said embodiments.

Certain features disclosed in the application are understood to be novel, including, for example, features either individually or in combination with other features as compared to the prior art.

LIST OF REFERENCE NUMERALS 1 first embodiment example
2 first arrangement
3 glass syringe
4 assembly element
5 protective cap part
6 glass syringe operating means
7 base body
8 syringe cone part
9 syringe needle
10 rear end
11 flange part
12 shoulder region
13 cylinder region
14 outer contour
15 securing means
16 inner contact area
18 distance
19 needle tip
20 spring elements
21 holding device
22 glass syringe operating means contact area
25 holding part
26 pushing element
27 plunger element
28 peripheral elevation
30 interface element
60 longitudinal extension
61 diameter
101 second embodiment example
102 arrangement
103 glass syringe
104 assembly element
105 protective cap part
107 base body
108 syringe cone part
109 syringe needle
111 flange part
112 shoulder region
113 cylinder region
114 outer contour
115 securing means 116 inner contact area
118 distance
119 needle tip
120 spring elements
121 holding device
122 glass syringe operating means contact area
128 peripheral elevation
130 interface element
134 first end surface of the spring elements
135 adhesive label
136 first grooves
137 second grooves
138 mounting area
160 longitudinal extension
161 diameter
203 glass syringe
139 second end surface of the spring elements
140 front surface of the assembly element
141 second surface of the assembly element
204 assembly element
207 base body
208 syringe cone part
209 syringe needle
210 rear end
211 flange part
212 shoulder region
213 cylinder region
214 outer contour
215 securing means
216 inner contact area
218 distance
219 needle tip
220 spring elements
221 holding device
222 glass syringe operating means contact area
236 rear area
260 longitudinal extension
261 diameter
301 further embodiment example
303 glass syringe
304 assembly element
309 syringe needle
312 shoulder region
314 outer contour
315 securing means
318 distance
319 needle tip
320 spring elements
321 holding device
322 glass syringe operating means contact area
323 first grooves
324 front surface of the assembly element
325 second surface of the assembly element
326 first end surface of the spring elements
327 second end surface of the spring elements
360 longitudinal extension
361 diameter
401 next embodiment example
403 glass syringe
404 assembly element
405 protective cap part
408 syringe cone part
409 syringe needle
414 outer contour
415 securing means
416 inner contact area
418 distance
419 needle tip
420 spring elements
421 holding device
422 glass syringe operating means contact area
423 first grooves
424 front surface of the assembly element
425 second surface of the assembly element
426 first end surface of the spring elements
427 second end surface of the spring elements
428 peripheral elevation
430 interface element
436 peripheral groove
440 attachment device
441 bulge
460 longitudinal extension
461 diameter
503 glass syringe
504 assembly element
505 protective cap part
508 syringe cone part
509 syringe needle
512 shoulder region
513 first grooves
514 front surface of the assembly element
515 second surface of the assembly element
516 first end surface of the spring elements
517 second end surface of the spring elements
520 spring elements
550 connecting web
551 predetermined breaking point
561 diameter

I claim:

1. A glass syringe-side assembly element for providing an interface element for a glass syringe, said glass syringe having a front side and a rear side and comprising on the front side a syringe cone part with a syringe needle and comprising on the rear side a flange part and a glass syringe operating means, wherein the assembly element is able to be arranged on an outer contour of the glass syringe,
wherein the assembly element comprises a securing means in order to secure the assembly element relative to the syringe needle in front of the flange part on the glass syringe in such a way that a reference point of the assembly element is always at a defined distance from a needle tip of the syringe needle,
wherein the assembly element comprises a holding device for holding the glass syringe operating means,
wherein the holding device is arranged on an outer peripheral side of the assembly element,
wherein the holding device comprises spring elements and first grooves, wherein the spring elements and first grooves are distributed on the outer peripheral side of the assembly element following a circumferential direction of the outer peripheral side, wherein the first grooves are each located between a respective two of said spring elements and are in direct contact with both of said two spring elements,
wherein the spring elements extend in a longitudinal direction of the holding device and interact with corresponding grooves extending in a longitudinal direction of the glass syringe operating means in the manner of a tongue-and-groove connection to reduce rotation of the assembly element, and
wherein the securing means is adhered to the outer contour of the glass syringe, by means of an adhesive label, or wherein the securing means is welded onto the outer contour of the glass syringe, wherein the glass syringe operating means comprises a holding part, on which a pushing element with a plunger element is mounted so as to move in a translatory manner.

2. The glass syringe-side assembly element according to claim 1, wherein the syringe cone part comprises a peripheral elevation and the assembly element further comprises a protective cap part for covering the syringe needle, the protective cap part able to be securely attached to the peripheral elevation.

3. The glass syringe-side assembly element according to claim 1, wherein the securing means comprises a mounting area for mounting a shoulder region of the glass syringe, in order to secure the assembly element to the shoulder region and thus to the glass syringe.

4. The glass syringe-side assembly element according to claim 1, wherein the securing means comprises a mounting area for mounting a cylinder region of the glass syringe, wherein the cylinder region has a longitudinal extension that is greater than a diameter of the cylinder region in order to secure the assembly element to the cylinder region and thus to the glass syringe.

5. The glass syringe-side assembly element according to claim 1, wherein the assembly element comprises a protective cap part for covering the syringe needle, which is arranged by means of a predetermined breaking point on the assembly element.

6. The glass syringe-side assembly element according to claim 1, wherein the holding device has a specific external structure in the form of a thread structure.

7. The glass syringe-side assembly element according to claim 6, wherein a counter structure to the specific external structure of the holding device is provided on the glass syringe operating means interacting with the specific external structure of the holding device.

8. The glass syringe-side assembly element according to claim 1, wherein the spring elements are projections that extend radially outward from an outer surface of the holding device and, in an axial direction of the assembly element, a first end surface of the spring elements is aligned with a front surface of the assembly element.

9. The glass syringe-side assembly element according to claim 8, wherein, in the axial direction of the assembly element, a second end surface of the spring elements is aligned with a second surface of the assembly element.

10. The glass syringe-side assembly element according to claim 1, wherein the holding device comprises second grooves being distributed on the outer peripheral side of the assembly element following the circumferential direction of the outer peripheral side.

11. The glass syringe-side assembly element according to claim 10, wherein the second grooves are located between each of said respective two of said spring elements and comprise a constant distance towards each of said respective two of said spring elements.

12. The glass syringe-side assembly element according to claim 1, wherein the assembly element flattens out towards a rear area.

13. A glass syringe-side assembly element for providing an interface element between a glass syringe and a glass syringe operating means,
wherein the assembly element can be arranged on an outer contour of the glass syringe, wherein the assembly element has an inner contact area facing the glass syringe and a glass syringe operating means contact area facing away from the glass syringe, wherein the inner contact area is configured to be softer than the glass syringe operating means contact area,
wherein the assembly element comprises a holding device for holding the glass syringe operating means, and wherein the holding device is arranged on an outer peripheral side of the assembly element, and
wherein the holding device comprises spring elements and first grooves, wherein the spring elements and first grooves are distributed on the outer peripheral side of the assembly element following a circumferential direction of the outer peripheral side, wherein the first grooves are each located between a respective two of said spring elements and are in direct contact with both of said two spring elements,
wherein the spring elements extend in a longitudinal direction of the holding device and interact with corresponding grooves extending in a longitudinal direction of the glass syringe operating means in the manner of a tongue-and-groove connection to reduce rotation of the assembly element, and
wherein the securing means is adhered to the outer contour of the glass syringe, by means of an adhesive label, or wherein the securing means is welded onto the outer contour of the glass syringe, wherein the glass syringe operating means comprises a holding part, on which a pushing element with a plunger element is mounted so as to move in a translatory manner.

14. The glass syringe-side assembly element according to claim 13, wherein the assembly element comprises a protective cap part for covering a syringe needle which is arranged by means of a predetermined breaking point on the assembly element.

15. The glass syringe-side assembly element according to claim 13, wherein the assembly element flattens out towards a rear area.

16. The glass syringe-side assembly element according to claim 13, wherein the spring elements are projections that extend radially outward from an outer surface of the holding device and, in an axial direction of the assembly element, a first end surface of the spring elements is aligned with a front surface of the assembly element.

17. The glass syringe-side assembly element according to claim 16, wherein, in the axial direction of the assembly element, a second end surface of the spring elements is aligned with a second surface of the assembly element.

18. The glass syringe-side assembly element according to claim 13, wherein the holding device comprises second grooves being distributed on the outer peripheral side of the assembly element following the circumferential direction of the outer peripheral side.

19. The glass syringe-side assembly element according to claim 18, wherein the second grooves are located between each of said respective two of said spring elements and comprise a constant distance towards each of said respective two of said spring elements.

20. A glass syringe-side assembly element for providing an interface element for a glass syringe, said glass syringe having a front side and a rear side and comprising on the front side a syringe cone part with a syringe needle and comprising on the rear side a flange part and a glass syringe operating means, wherein the assembly element is able to be arranged on an outer contour of the glass syringe,
wherein the assembly element comprises a securing means in order to secure the assembly element relative to the syringe needle in front of the flange part on the glass syringe in such a way that a reference point of the assembly element is always at a defined distance from a needle tip of the syringe needle, wherein the assembly element comprises a holding device for holding the glass syringe operating means, wherein the holding device is arranged on an outer peripheral side of the assembly element, and wherein the holding device comprises spring elements and first grooves, wherein the spring elements and first grooves are distributed on the outer peripheral side of the assembly element following a circumferential direction of the outer peripheral side, wherein the first grooves are each located between a respective two of said spring elements and are in direct contact with both of said two spring elements, wherein the spring elements extend in a longitudinal direction of the holding device and interact with corresponding grooves extending in a longitudinal direction of the glass syringe operating means in the manner of a tongue-and-groove connection to reduce rotation of the assembly element, wherein the securing means is adhered to the outer contour of the glass syringe, by means of an adhesive label, or wherein the securing means is welded onto the outer contour of the glass syringe, wherein the glass syringe operating means comprises a holding part, on which a pushing element with a plunger element is mounted so as to move in a translatory manner wherein the outer peripheral side of the assembly element is in contact only with the glass syringe operating means and/or with a protective cap part, wherein an inner peripheral side of the assembly element is in contact only with the glass syringe, and wherein the assembly element is arranged on only one side of the flange part facing towards the syringe cone part.

21. The glass syringe-side assembly element according to claim 20, wherein the assembly element flattens out towards a rear area.

22. The glass syringe-side assembly element according to claim 20, wherein the spring elements are projections that extend radially outward from an outer surface of the holding device and, in an axial direction of the assembly element, a first end surface of the spring elements is aligned with a front surface of the assembly element.

23. The glass syringe-side assembly element according to claim 22, wherein, in the axial direction of the assembly element, a second end surface of the spring elements is aligned with a second surface of the assembly element.

24. The glass syringe-side assembly element according to claim 20, wherein the holding device comprises second grooves being distributed on the outer peripheral side of the assembly element following the circumferential direction of the outer peripheral side.

25. The glass syringe-side assembly element according to claim 24, wherein the second grooves are located between each of said respective two of said spring elements and comprise a constant distance towards each of said respective two of said spring elements.

* * * * *